United States Patent
US 6,927,393 B2
Cotte et al.
Aug. 9, 2005

(54) METHOD OF IN SITU MONITORING OF SUPERCRITICAL FLUID PROCESS CONDITIONS

(75) Inventors: John M. Cotte, New Fairfield, CT (US); Kenneth J. McCullough, Fishkill, NY (US); Wayne M. Moreau, Wappingers Falls, NY (US); Keith R. Pope, Danbury, CT (US); Robert J. Purtell, Mohegan Lake, NY (US); John P. Simons, Wappingers Falls, NY (US); Charles J. Taft, Wappingers Falls, NY (US)

(73) Assignee: International Business Machines Corporation, Armonk, NY (US)

( * ) Notice: Subject to any disclaimer, the term of this patent is extended or adjusted under 35 U.S.C. 154(b) by 225 days.

(21) Appl. No.: 10/320,835

(22) Filed: Dec. 16, 2002

(65) Prior Publication Data

US 2004/0113079 A1 Jun. 17, 2004

(51) Int. Cl.$^7$ ................................. G01J 5/02
(52) U.S. Cl. ................ 250/339.13; 250/339.12; 250/339.06; 250/339.01; 250/338.1; 250/336.1
(58) Field of Search ............... 250/339.13, 339.12, 250/339.06, 339.01, 338.1, 336.1

(56) References Cited

U.S. PATENT DOCUMENTS

| | | | |
|---|---|---|---|
| 4,297,577 A | 10/1981 | Coe et al. | |
| 5,451,787 A | * 9/1995 | Taylor | 250/338.5 |
| 5,614,718 A | 3/1997 | Brace | |
| 5,777,726 A | * 7/1998 | Krone-Schmidt | 356/38 |
| 5,793,042 A | 8/1998 | Quick | |
| 6,188,475 B1 | 2/2001 | Inman et al. | |
| 6,258,978 B1 | 7/2001 | Kitchen et al. | |
| 6,391,385 B1 | * 5/2002 | Holst et al. | 427/250 |
| 6,454,869 B1 | * 9/2002 | Cotte et al. | 134/2 |
| 6,465,775 B2 | 10/2002 | Mullins et al. | |
| 6,596,093 B2 | * 7/2003 | DeYoung et al. | 134/36 |
| 6,617,175 B1 | * 9/2003 | Arno | 438/7 |
| 2004/0058488 A1 | * 3/2004 | Arno | 438/200 |

* cited by examiner

*Primary Examiner*—David Porta
*Assistant Examiner*—Christine Sung
(74) *Attorney, Agent, or Firm*—DeLio & Peterson, LLC; John J. Tomaszewski; Lisa U. Jaklitsch

(57) ABSTRACT

A method and apparatus are provided for in situ monitoring and analyzing of process parameters for semiconductor fabrication processes including cleaning semiconductor wafers utilizing a supercritical fluid or a high pressure liquid such as $CO_2$. The method and apparatus utilize a spectrometer having a reflective mirror proximate the vessel holding the high pressure fluid. NIR radiation transmitted into the vessel through a window and out of the vessel through an opposed window is reflected and detected and measured and the composition of the fluid in the pressure vessel is determined allowing the user to control process parameters based on the measured composition.

12 Claims, 1 Drawing Sheet

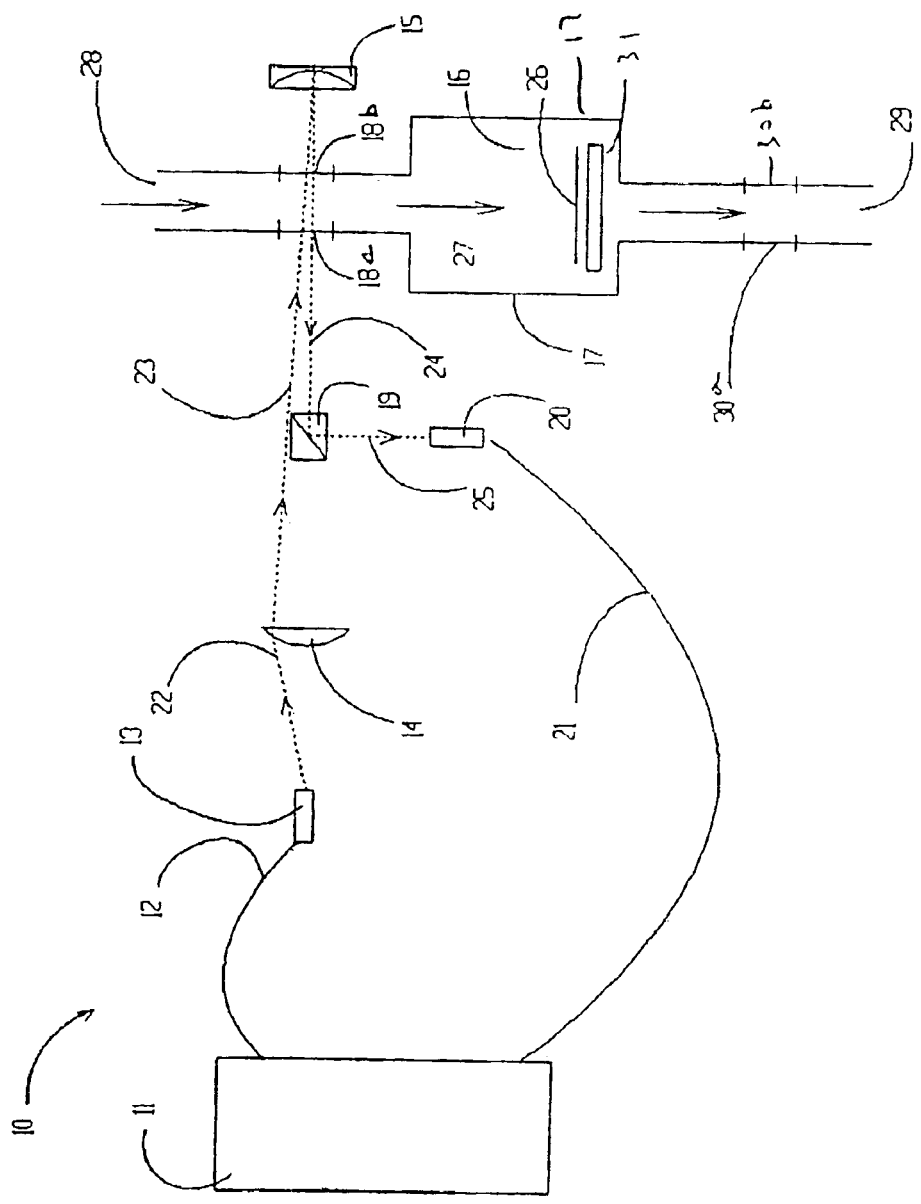
Figure ative Art

Semiconductor integrated circuits (IC's) are fabricated by a series of process steps many of which involve the use of gaseous and liquid materials. Included among such processes are etching, diffusion, chemical vapor deposition (CVD), ion implantation and the like. One important fabrication step is to clean semiconductor wafers and other IC's using a supercritical fluid or high pressure liquid and the monitoring of process conditions is important for process optimization. For example, if a co-solvent is used with the supercritical fluid/high pressure liquid, it is important to know the amount of co-solvent in the mixture during the process so that the mixture can be maintained at an optimal pre-determined concentration.

It is also important to measure the composition of the effluent to determine, among other things, the process endpoint. By monitoring both the input mixture and effluent and the composition of the supercritical fluid or high pressure liquid, the amount of co-solvent used in the process can be determined as well as numerous other operating parameters dependent upon concentration. When monitoring for endpoint verification, the effluent composition will reflect the cessation of removal of material from the workpiece or, in the case of a deposition process, the deposition material (from the co-solvent) and the effluent concentration will increase reflecting a cessation of deposition on the surface of the workpiece.

The present invention has been developed for its applicability for the semiconductor and microelectronics fabrication industries and, in particular, to the cleaning of contaminated substrates, including, for example, semiconductor wafers, multiple chip carriers, flat panel displays, magnetic hard disks and other electronic devices. Many methods have been developed to clean such surfaces and techniques include the use of solvents or chemicals, high energy sonic waves, cryogenic aerosols and combinations thereof.

The use of supercritical carbon dioxide and other supercritical fluids as well as densified liquids are now being used for cleaning semiconductor wafers. Liquid or supercritical carbon dioxide has very low surface tension, high diffusivity, solvent like properties, and no adverse environmental effects. Finally, no residual liquid remains on the precision surface, since carbon dioxide returns to its gas phase after process completion.

Unfortunately, monitoring and analyzing of supercritical fluids or high pressure liquids is very difficult, especially in situ, and such a monitoring process would have many advantages in process costs, cycle time and process repeatability.

Most conventional analysis equipment falls into the category where sampling is first effected and the sample passed to the analyzer. The analyzer normally embodies any one of the many known techniques for analysis such as photometry, spectroscopy, filter reduction and chromatography. The major disadvantage of such techniques lies in the sampling since the analyzers themselves are usually adequate whereas the sampling systems generally require a considerable amount of maintenance and are known to be unreliable.

Many processes require, or would at least benefit from, on-line monitoring of the chemical composition and/or other parameters of the reactant mixtures involved. Such in situ analysis entails a number of significant advantages over other techniques particularly in that all of the problems associated with sampling and sample handling are inherently eliminated. It also permits dynamic monitoring of chemical and/or physical changes that occur during the course of the process.

As far as is known, very few (if any) of the forms of instrumentation heretofore available are useful or satisfactory for the on-line analysis of supercritical fluid streams and high pressure liquids, as well as their mixed phases. In particular, it is not believed that any such instrumentation is capable of measuring quantitative chemical composition data for supercritical fluid and/or high pressure liquid streams, especially in a reactive environment.

Optical analyses of fluids, including gases, are well known, and various optical and spectroscopic techniques have been applied in industrial processes. In general, light is directed at the sample and the light spectrum of the reflected light (absorbance spectra) is detected and the detected spectra are fit to known spectra to obtain information regarding the composition of the tested material.

Bearing in mind the problems and deficiencies of the prior art, it is therefore an object of the present invention to provide a method for in situ monitoring and analyzing of process fluids and/or liquids and other parameters in the fabrication of semiconductor and microelectronic components where a supercritical fluid and/or high pressure liquids are used.

It is another object of the present invention to provide an apparatus for the in situ monitoring and analyzing of process fluids and/or liquids and other parameters in the fabrication of semiconductor and microelectronic components where supercritical fluids and/or high pressure liquids are used.

Still other objects and advantages of the invention will in part be obvious and will in part be apparent from the specification.

SUMMARY OF THE INVENTION

The above and other objects and advantages, which will be apparent to one of skill in the art, are achieved in the present invention which is directed to, in a first aspect, a method for the in situ monitoring and analyzing of parameters in the fabrication of electronic components such as semiconductor wafers comprising the steps of:

providing a pressure vessel with opposed windows for transmission of an infrared light beam into and out of the vessel, the beam passing through the inside of the vessel;

providing a workpiece, such as an electronic component article, to be treated in the vessel;

providing one or more materials in the vessel for treating the substrate including a supercritical fluid, a high pressure liquid and optionally containing one or more solvents;

providing an infrared spectrometer for generating and transmitting a beam of infrared light over a range of wavelengths through one of the windows into the pressure vessel, through the material contained in the vessel and out the opposed window;

providing a reflective transmission mirror;

providing a receiver for receiving reflected infrared light from the reflective transmission mirror;

passing an infrared beam of light at a particular wavelength through one of the windows into the vessel, passing the beam through the vessel and out the opposed window at the reflective transmission mirror and receiving the reflected light beam in the receiver;

detecting and analyzing the reflected infrared light;

repeating the above over a desired wavelength range; and determining the composition of the material and other parameters in the vessel based on the detection and analysis of the reflected light beams.

In another aspect of the present invention, an apparatus is provided for the in situ monitoring and analyzing of parameters in the fabrication of electronic components such as semiconductor wafers comprising:

a pressure vessel with opposed windows for transmission of an infrared light beam into and out of the vessel, the beam passing through the inside of the vessel;

means for supplying one or more materials in the vessel for treating a substrate workpiece including a supercritical fluid, a high pressure liquid and optionally containing one or more solvents or reagents;

an infrared spectrometer for generating and transmitting a beam of infrared light over a range of wavelengths through one of the windows into the pressure vessel, the beam passing through the vessel and out the opposed window;

a reflective transmission mirror proximate the opposed window;

a receiver for receiving reflected infrared light from the reflective transmission mirror;

means for passing an infrared beam of light at a particular wavelength through one of the windows into the vessel, through the vessel and out the opposed window at the reflective transmission mirror and receiving the reflected light beam in the receiver; and means for detecting and analyzing the reflected infrared light;

wherein when beams over a desired wavelength range are transmitted and reflected and detected and analyzed the composition of the material in the vessel is determined based on the detection and analysis of the reflected light beams.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which the FIGURE is a schematic diagram of an apparatus of the invention.

DESCRIPTION OF THE PREFERRED EMBODIMENT(S)

In describing the preferred embodiment of the present invention, reference will be made herein to the FIGURE. Features of the invention are not necessarily shown to scale in the drawings.

A method and apparatus are provided to determine simultaneously the chemical composition, pressure and temperature of a supercritical fluid or high pressure liquid at pressures up to 20,000 psi in situ in a vessel with a single measurement by passing an infrared beam through opposed vessel windows using a solid state scannable spectrometer. The method and apparatus requires only a single reflective surface and a minimum path of about 2 mm. Using the method and apparatus of the invention concentrations of the supercritical fluid or high pressure liquid and other chemical components of the cleaning mixtures may be determined by NIR (near infrared) in a high pressure environment. For convenience the following will be directed to carbon dioxide although other such materials may be used as will be appreciated by those skilled in the art.

In general, the invention involves the use of near-infrared (NIR) absorption spectroscopy to detect the amount of solvent or other chemical in a material such as supercritical carbon dioxide and/or high pressure carbon dioxide in a pressure vessel. The fraction of light absorbed per unit path length depends on the composition of the carbon dioxide mixture in the pressure vessel and the wavelength of the light. Thus, the amount of absorption as a function of wavelength of light, hereinafter referred to as "absorption spectrum", will be used as an indicator to determine the composition of the mixture in the pressure vessel. Pressure and temperature of the composition are also determined by standard high pressure monitoring and co-injection devices including analysis of peak shifting and pressure broadening.

In general, the NIR absorption spectra show optical density, which is a logarithmic scale measure of the ratio of incident light to light transmitted through the composition plotted as a function of wave length. An optical density of 0 means that all the incident light at that wave length is transmitted through the composition and none absorbed, and an optical density of 1, means that about 90% of the incident light at that wave length is absorbed.

The absorption spectrum of carbon dioxide ($CO_2$) shows large absorption peaks in the range of about 900 nm to 1600 nm.

The spectra will be taken at the high pressures in the vessel which is maintained at about room temperature up to 150° C. While the spectral features of absorption spectra of gases generally vary with temperature and pressure, at the high pressures in the pressure vessel the absorption spectra essentially lose their dependence on temperature and pressure for purposes of this invention.

Spectral analysis may be accomplished by comparing the intensities of the detected absorption indications with known absorption spectra of carbon dioxide-solvent gas mixtures having different relative mass fractions. The detected absorption indications may be fit to the known spectra using, for example, a least means squares fitting, multivariate analysis, etc. In another embodiment, the detected absorption indication may be analyzed in terms of fractional peak areas and correlated with mass fraction using known spectral data.

In general, the goal of using NIR in the present invention is to determine changes in the intensity of the beam of incident radiation as a function of wave length or frequency after it interacts with the $CO_2$ composition in the vessel. The function of the infrared spectrometer is to disperse the light from a broad band infrared source so that its intensity at each frequency can be measured and analyzed. The ratio of the intensity of the light beam before and after the light beam interacts with the material is determined and a plot of this ratio vs. frequency is known as the infrared spectrum. Use of a spectrometer provides real-time information and data that is useful in determining what compositional changes have occurred and when these changes have occurred in the pressure vessel. Any conventional spectrometer may be used such as those sold by Brimrose.

The infrared spectrometer's main purpose is to determine optical intensity vs. frequency or wave length. It needs a light source, a means to set or measure wave lengths, a detector and a device to record the spectrum. The spectrometer determines the changes in the intensity of a beam of infrared radiation as a function of frequency (wave number) after it interacts with the material under observation. The spectrometer disperses the light from a broad band infrared source and measures the intensity at each frequency. The ratio of intensity before and after the light interaction of the mixture sample is determined and a plot of this ratio vs. frequency is the infrared spectrum.

In accordance with the teachings of the present invention, the change in infrared intensity results from the absorbance at specific frequencies by chemicals, particularly carbon dioxide and solvents dispersed in the carbon dioxide, which exists in the pressure vessel during the semiconductor fabrication process such as a wafer cleaning process being performed in the vessel using supercritical or high pressure $CO_2$. The spectrometer is actually measuring the intensity of the remaining light (reflected light) after absorption by the composition at each frequency. The output intensity from the interaction is eventually measured by the detector. The output intensity information is sent back to the spectrometer to determine the intensity ratio. The data is typically utilized in a computer where the data are analyzed to provide the composition of the mixture.

Referring now to the FIGURE, an apparatus of the invention is shown in general as numeral 10. A spectrometer 11 provides a light source over a number of wavelengths through source fiber 12. The light beam is directed by lens 13 to an achromatic lens 14 which provides a single wavelength beam of incident light 23. A pressure vessel 16 has walls 17 and opposed windows 18a and 18b in the walls 17 facing the incident beam of light 23. A $CO_2$ supercritical fluid containing composition is shown therein as numeral 27 and passes through the vessel 16 from the inlet 28 to the outlet 29 as shown by the arrows. The beam of light 22 from the source lens 13 is directed through the achromatic lens 14 as incident beam of light 23 which is directed into the pressure vessel 16 through window 18a and through fluid mixture 27 and out opposed window 18b at mirror 15. The achromatic lens 14 has a focal length which is focused on mirror 15. A semiconductor wafer substrate is shown as numeral 26 and is positioned on support 31. The vessel 16 has an inlet 28 and an outlet 29. Opposed windows 18a and 18b are in the inlet 28. Opposed windows 30a and 30b are in outlet 29.

The incident light beam 23 is reflected off mirror 15 and is reflected back in window 18b through the vessel and out of the vessel through window 18a as reflected beam 24. This reflected beam 24 is directed by a 45° mirror 19 as reflected beam 25 into receiver lens 20. The receiver lens 20 transmits the reflected light beam to the spectrometer 11 through receiver fiber 21. Spectrometer 11 analyzes the incident beam 23, reflected beam 25 and wavelength and plots the intensity versus wavelength for a number of wavelengths over the NIR range. The spectrum is compared to known spectra and the composition of the mixture is determined. Depending on the composition in the vessel, the parameters of the reaction can be changed such as by increasing the solvent composition of the $CO_2$ mixture, adjusting operating parameters such as temperature and pressure, etc. The apparatus described is shown as a monitor for the inlet stream and can be repeated for the outlet stream utilizing windows 30a and 30b. The comparison of the two is one means for determining the end point for a process. Additionally, this apparatus may be limited to just monitoring the outlet stream alone to determine the end point of a process. Opposed windows can also be proximate the workpiece 26 for monitoring the material 27 in the main body of the pressure vessel.

In another embodiment, reflected beam 24 (off mirror 15) can be directed directly to receiver lens 20 without passing back through pressure vessel 16.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A method for the insitu monitoring and analyzing of parameters in the fabrication of electronic components comprising the steps of:
   providing a pressure vessel with opposed windows for transmission of an infrared light beam into and out of the vessel, the beam passing through the inside of the vessel;
   providing a workpiece to be treated in the vessel;
   providing one or more materials in the vessel for treating the substrate including a supercritical fluid, a high pressure liquid and optionally containing one or more solvents;
   providing an infrared spectrometer for generating and transmitting a beam of infrared light over a range of wavelengths through one of the windows into the pressure vessel, through the material contained in the vessel and out the opposed window;
   providing a reflective transmission mirror;
   providing a receiver for receiving reflected infrared light from the reflective transmission mirror;
   passing an infrared beam of light at a particular wavelength through one of the windows into the vessel, passing the beam through the vessel and out the opposed window at the reflective transmission mirror and receiving the reflected light beam in the receiver;
   detecting and analyzing the reflected infrared light;
   repeating the above over a desired wavelength range; and
   determining the composition of the material and other parameters in the vessel based on the detection and analysis of the reflected light beams.

2. The method of claim 1 wherein the workpiece is an integrated circuit.

3. The method of claim 2 wherein the material in the vessel includes $CO_2$.

4. The method of claim 3 wherein the $CO_2$ is in the supercritical state.

5. The method of claim 1 wherein the reflected light beam passes back through the pressure vessel and is then received in the receiver.

6. The method of claim 1 wherein the composition of the material is determined at an inlet to the vessel.

7. The method of claim 1 wherein the composition of the material is determined at an outlet of the vessel.

8. The method of claim 1 wherein the composition of the material is determined proximate the workpiece.

9. An apparatus for the insitu monitoring and analyzing of parameters in the fabrication of electronic components comprising:

- a pressure vessel with opposed windows for transmission of an infrared light beam into and out of the vessel, the beam passing through the inside of the vessel;
- means for supplying one or more materials in the vessel for treating a substrate workpiece including a supercritical fluid, a high pressure liquid and optionally containing one or more solvents or reagents;
- an infrared spectrometer for generating and transmitting a beam of infrared light over a range of wavelengths through one of the windows into the pressure vessel, the beam passing through the vessel and out the opposed window;
- a reflective transmission mirror proximate the opposed window;
- a receiver for receiving reflected infrared light from the reflective transmission mirror;
- means for passing an infrared beam of light at a particular wavelength through one of the windows into the vessel, through the vessel and out the opposed window at the reflective transmission mirror and receiving the reflected light beam in the receiver; and
- means for detecting and analyzing the reflected infrared light;
- wherein when beams over a desired wavelength range are transmitted and reflected and detected and analyzed the composition of the material in the vessel is determined based on the detection and analysis of the reflected light beams.

10. The apparatus of claim 9 wherein the workpiece is an integrated circuit.

11. The apparatus of claim 10 wherein the material in the vessel is $CO_2$.

12. The apparatus of claim 11 wherein the $CO_2$ is in the supercritical state.

* * * * *